(12) United States Patent
Maeda et al.

(10) Patent No.: US 6,632,668 B2
(45) Date of Patent: Oct. 14, 2003

(54) MONOLAYER SHEET STRUCTURE OF PRIMARY HEPATOCYTES OBTAINED USING A PROTEIN-PHOSPHORYLATION INHIBITOR

(75) Inventors: Sumio Maeda, Aichi (JP); Hidetoshi Inagaki, Aichi (JP); Takao Saito, Aichi (JP)

(73) Assignee: Japan as represented by the Secretary of Agency of Industrial Science and Technology, Tokyo (JP)

( * ) Notice: Subject to any disclaimer, the term of this patent is extended or adjusted under 35 U.S.C. 154(b) by 0 days.

(21) Appl. No.: 09/748,186

(22) Filed: Dec. 27, 2000

(65) Prior Publication Data

US 2001/0055806 A1 Dec. 27, 2001

(30) Foreign Application Priority Data

Jun. 7, 2000 (JP) ......................................... 2000-170040

(51) Int. Cl.[7] .............................. C12N 5/06; C12N 5/08; C12N 11/02

(52) U.S. Cl. ...................... 435/395; 424/93.7; 435/177; 435/325; 435/375; 435/384; 435/385

(58) Field of Search .................................. 435/177, 325, 435/375, 384, 385, 395; 424/93.7

(56) References Cited

PUBLICATIONS

Sumio Maeda, et al. "Staurosporine Promotion of Formation of Continuous Monolayers of Primary Rat Hepatocytes by Improving Attachment and Spreading", Biosci. Biotechnol. Biochem., vol. 64, No. 9, 2000, pp. 1985–1987.

*Primary Examiner*—David M. Naff
(74) *Attorney, Agent, or Firm*—Oblon, Spivak, McClelland, Maier & Neustadt, P.C.

(57) ABSTRACT

A monolayer sheet structure is prepared containing a confluent monolayer of primary hepatocytes cultured on a substrate in sheet form. The monolayer sheet structure is formed by treating the hepatocytes in the monolayer formation stage with a protein-phosphorylation inhibitor having an indolo [2,3-a] carbazole structure, such as staurosporine, or other similar structure.

18 Claims, 2 Drawing Sheets

MONOLAYER SHEET STRUCTURE OF PRIMARY HEPATOCYTES OBTAINED USING A PROTEIN-PHOSPHORYLATION INHIBITOR

BACKGROUND OF THE INVENTION

1. Field of the Invention

This invention relates to a monolayer sheet structure of primary hepatocytes, and a method of manufacturing it, and more particularly, to a method of forming a confluent monolayer sheet structure of primary hepatocytes so as to allow a dramatic improvement in the adhesion (attachment) and extension (spreading) of primary hepatocytes on to the culture substrate, and to the monolayer sheet structure formed by such a method.

This invention falls into the category of elemental technology for the systems engineering needed to construct artificial internal organs and bioreactors using cells, and is particularly useful as a technique for forming cell aggregates.

2. Description of the Related Art

The most widely used conventional technique for forming monolayers of primary hepatocytes is the simple method which consisting of suspending isolated primary hepatocytes in animal cell culture medium containing various bioactive hormones (such as dexamethasone) or serum, and spreading them on a culture substrate (such as a plastic laboratory dish coated with collagen, etc.), after which they are subjected to standing culture for a few hours to 24 hours. However, the monolayer structure of hepatocytes formed by this method becomes intermittently linked patch-like discontinuous monolayers of one to tens of cells, rather than a so-called confluent monolayer sheet structure, which is continuous and without gaps. Even from this state, a confluent state might be achieved through cell proliferation in the case of other cells, but primary hepatocytes do not proliferate easily, making it impossible to subsequently form a confluent sheet structure from the monolayer sheet structure formed during the first 24 hours.

Under these circumstances, and reflecting on prior art as described above, the present inventors discovered as a result of exhaustive research that the adhesion and extension of primary hepatocytes on to a culture substrate could be dramatically enhanced by treatment thereof with a suitable amount of a protein-phosphorylation inhibitor having an indolo [2,3-a] carbazole skeleton (typical example: staurosporine) during formation of the primary hepatocytes monolayers according to prior art, and achieved this invention by exploiting this effect.

SUMMARY OF THE INVENTION

The present invention provides a monolayer sheet structure of primary hepatocytes that could not be formed by conventional cell layer formation technology, along with a simple method of forming such a monolayer sheet structure.

This invention is a monolayer sheet structure formed as a confluent monolayer of primary hepatocytes cultured on a culture substrate, said monolayer sheet structure is formed by treating the hepatocytes with a protein-phosphorylation inhibitor having an indolo [2,3-a] carbazole or other similar structure in the monolayer formation stage.

This invention is aimed at providing a confluent monolayer sheet structure of primary hepatocytes, that could not be formed with conventional cell monolayer formation technology, and also providing a simple method of forming such a structure.

Furthermore, this invention is also aimed at providing a method of manufacturing a monolayer sheet structure of primary hepatocytes using a protein-phosphorylation inhibitor (compound) with an indolo [2,3-a] carbazole or other similar skeleton, and also providing a monolayer sheet structure manufactured according to said method.

This invention, which is to solve the subjects described above, comprises the following technological means.

(1) A monolayer sheet structure consisting of a confluent monolayer formed from primary hepatocytes cultured on a culture substrate,
said monolayer sheet structure of primary hepatocytes is produced by treating the hepatocytes with a protein-phosphorylation inhibitor having an indolo [2,3-a] carbazole or similar skeleton in the step of formation of the monolayer.

(2) The monolayer sheet structure of primary hepatocytes according to (1) above, wherein the monolayer sheet structure is produced by treating the hepatocytes with staurosporine.

(3) A method of manufacturing a monolayer sheet structure by culturing primary hepatocytes on a culture substrate to produce a confluent monolayer, which comprises treating the hepatocytes with a protein-prosphorylation inhibitor having an indolo [2,3-a] carbazole or similar skeleton in the step of formation of the monolayer to form the monolayer sheet structure of primary hepatocytes.

(4) The method of manufacturing a monolayer sheet structure of primary hepatocytes according to (3) above, wherein the hepatocytes are treated with staurosporine to form the monolayer sheet structure of primary hepatocytes.

DESCRIPTION OF THE PREFERRED EMBODIMENTS

Figure 1A:
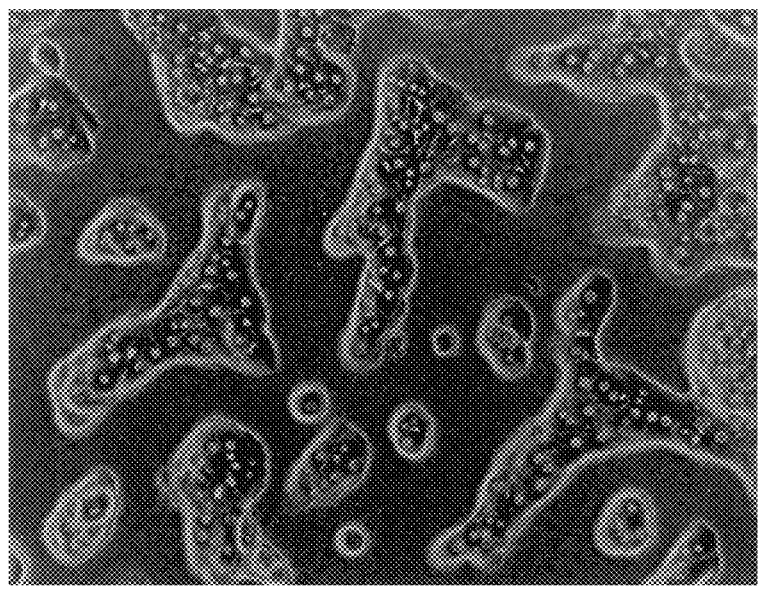
FIG. 1 shows a phase contrast microscope image of monolayer of primary cultured hepatocytes of prior art (A) and monolayer of primary cultured hepatocytes of this invention (B)

Next, this invention is explained further in more detail.

Conventional techniques for forming monolayers of primary hepatocytes as well as partial variations on such techniques have been described in detail, for example in "Test Methods for Primary Cultured Hepatocytes" by Toshikazu Nakamura, Gakkai Shuppan Center, 1987, and "Isolated hepatocytes preparation, properties and applications" by M. N. Berry, A. M. Edwards and G. J. Barritt, eds. in Elsevior, 1991.

A representative method is that 1) isolating primary hepatocytes from livers or liver sections by a method such as collagenase perfusion method, 2) suspending them in an animal cell culture medium (such as Williams' E medium, Dulbecco's modified eagle's medium and the like) containing various physiological active hormones (such as dexamethasone and the like) or a few percent to about 10% serum, 3) seeding them on a culture substrate (such as a plastic laboratory dish coated with collagen, etc.) and subjecting them to standing culture for a few to 24 hours, and 4) in many cases, inserting a medium exchange operation after several hours of the seeding of the cells in the step of the standing culture.

In this invention, these methods can be used for monolayer formation of primary hepatocytes in addition to treatment of the cells with a protein-phosphorylation inhibitor having an indolo [2,3-a] carbazole or other similar skeleton.

One compound that typifies the protein-phosphorylation inhibitor having an indolo [2,3-a] carbazole or other similar skeleton used in this invention is staurosporine, the structural formula of which is given here: Standard nomenclature [9S-(9a,10b,11b,13a)]-9,13-epoxy-2,3,10,11,12,13-hexahydro-10-methoxy-9-methyl-11-(methylamino)-1H, 9H-diindolo[1,2,3-gh:3',2',1'-1m]pyrrolo[3,4-j][1,7] benzodiazonin-1-one; chemical formula $C_{28}H_{26}N_4O_3$, molecular weight 466. Biochemically, it is known to exhibit inhibitory action against the activity of various protein kinases such as protein kinase C by competitive inhibition of ATP binding. Its effects on cells are known to include inducing differentiation, inducing apoptosis and inhibiting platelet aggregation and the like (Biochemical Dictionary, $3_{rd}$ Ed., Tokyo Kagaku Dojin, 1998; Omura, S. et al., J Antibiot (Tokyo), 48, 535–548, (1995)).

In this invention, preferably the staurosporine described above is used, but it is also possible to use another protein-phosphorylation inhibitor (compound) having an indolo [2,3-a] carbazole or other similar skeleton. Examples are the published substances K252a, K252b, KT5720 and KT5823 (these described for example in the Journal of Cellular Physiology, 179:179–192 (1999), No. 180, Page 182) or KT5926, GF109203X, Ro31-8425, UCN-01, UCN-01-Me, RK-286C, CGP41251 (these described for example in The Journal of Antibiotics, Vol. 48, No. 7, p535–548, No. 536, FIG. 1).

In this invention, the protein-phosphorylation inhibitor having an indolo [2,3-a] carbazole or other similar skeleton is defined as meaning a substance that exhibits protein inhibition activity, and which is a compound having an indolo [2,3-a] carbazole (IC) skeleton, a derivatives of such a compound, or a compound having a skeleton similar to an IC skeleton.

[Chemical Formula 1]

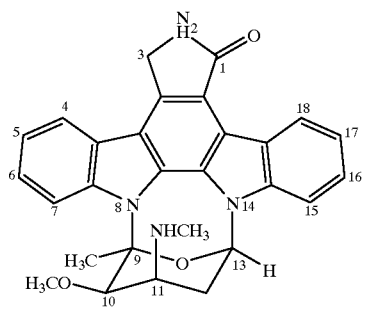

In this invention, it is possible to form a confluent monolayer sheet structure of primary hepatocytes within 24 hours by the simple operation of adding a protein-phosphorylation inhibitor (staurosporine) having an indolo [2,3-a] carbazole or other similar skeleton to the medium in the appropriate stages of the method of primary hepatocytes monolayer formation which are described in the above as the stages of 2) the stage of suspending primary hepatocytes in medium in the method of forming monolyer of primary hepatocytes, 3) the stage of subjecting them to standing culture after seeding the cells on a culture substrate, and 4) the stage of exchanging of the medium.

In the embodiment described above, the protein-phosphorylation inhibitor (staurosporine) having an indolo [2,3-a] carbazole or other similar skeleton can be dissolved directly in a medium to be used, or else a prepared stock solution of the inhibitor in an organic solvent such as dimethylsulfoxide and the like can be diluted in a medium to be used.

In the embodiment described above, the protein-phosphorylation inhibitor (staurosporine) having an indolo [2,3-a] carbazole or other similar skeleton is usually used at a final concentration of about 10 nM–100 nM, but is not limited to this range.

In the embodiment described above, "primary hepatocytes" refers to hepatocytes or liver parenchymal cells isolated from livers, and while those derived from mammals such as rats or humans can be used, they are not limited to these examples.

EXAMPLES

The present invention is described below through examples, but this invention is not limited in any way by the following examples.

Example 1

In order to isolate primary hepatocytes, rat livers were used and primary hepatocytes were isolated from the rat livers by ordinary methods, that was, by collagenase perfusion followed method and four subsequent low-speed centrifuge isolation. The hepatocytes were suspended in an animal cell culture medium (Williams' E medium) containing 10 nM Dexamethasone and 10% fetal bovine serum, and seeded at a cell concentration of $10 \times 10^4$ cell/cm$^2$ on 6-well cell culture plastic plates coated with type I collagen. For the samples to be treated, staurosporine was added to the medium to a final concentration of 50 nM. Next, they were subjected to standing culture for 4 hours at 37° C. in a $CO_2$ incubator in the presence of 5% (v/v) $CO_2$, and the medium was replaced with Williams' E medium containing 10 nM insulin, 10 nM dexamethasone and 0.7 μg/ml aprotinin. For the samples to be treated, staurosporine was again added to the medium to a final concentration of 50 nM. Finally, after the standing culture for 20 hours, the condition of the cells was observed through a phase contrast microscope. The results are shown in FIG. 1.

Figure 1B:
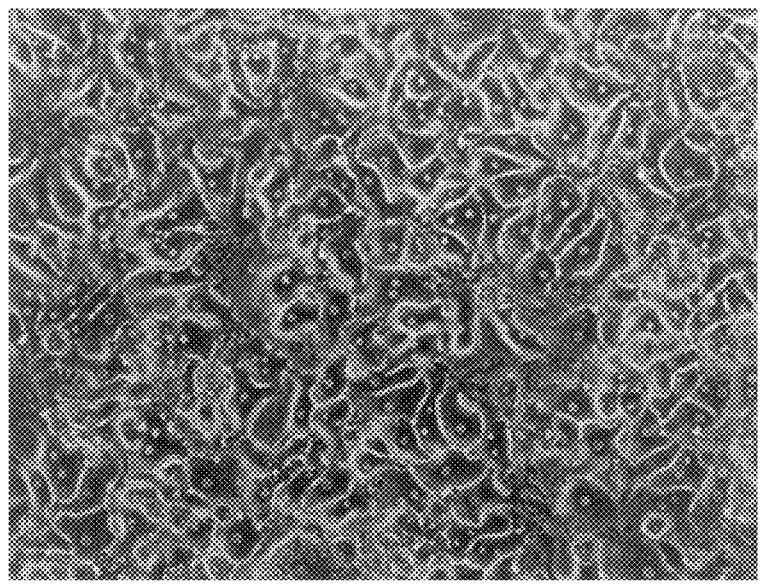

In FIG. 1, A shows a phase contrast microscope image (magnification:×200) of primary cultured hepatocytes monolayer made by conventional methods (without staurosporine), while B shows an image of the primary cultured hepatocytes monolayer of this invention (with 50 nM staurosporine).

The results in FIG. 1 show clearly that in the case of the hepatocytes not treated with staurosporine, cell aggregates are formed, which comprises intermittently linked patch-like discontinuous monolayers of one to tens of cells. On the other hand, in the case of the hepatocytes treated with staurosporine, adhesion (attachment) and extension (spreading) thereof is improved, and cell aggregates are formed, which comprises a confluent continuous monolayer sheet of closely adjoining cells.

Example 2

Figure 2:
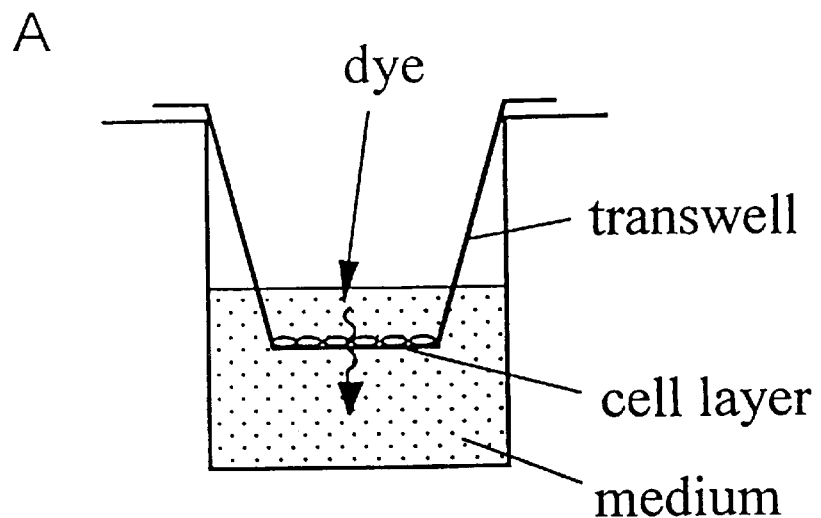
FIG. 2 shows a schematic explanatory drawing (A) of a dye permeation assay using transwell filters, and (B) of the results of the assay.
Figure 2:
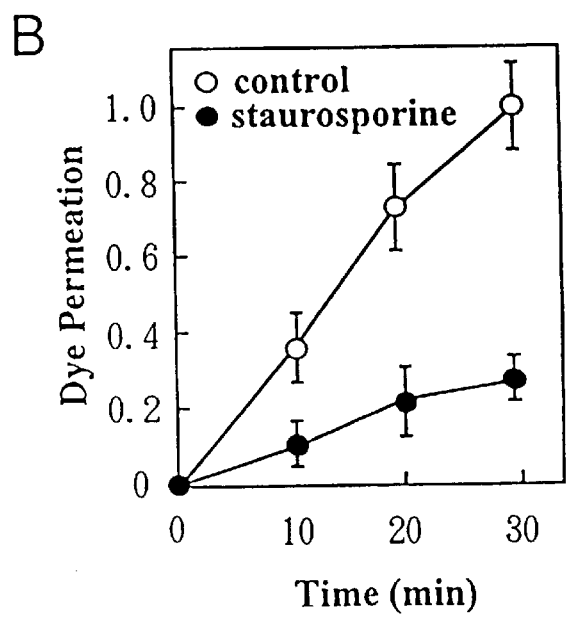

In parallel with Example 1 above, primary rat hepatocytes were seeded on transwell filters (3-micron pore polytetrafluoroethylene coated with type I collagen) suitable to 24-well cell culture plates, and differences in the tightness of the cell monolayer structure produced by staurosporine treatment were measured by a dye permeation assay. In FIG. 2,A shows a schematic explanatory drawing of a dye permeation assay using transwell filters, while in FIG. 2,B shows results of the assay.

In the dye permeation assay using transwell filters shown in A of FIG. 2, primary hepatocytes were seeded on transwell filters installed in wells on 24-well cell culture plates, and after the monolayer thereof was formed, 20 μl of dye (0.25% bromphenol-blue dye) was added to the upper liquid layer (medium) on the filter. 50 μl samples were then taken with the passage of time from the lower liquid layer (medium) on the filter at a constant temperature of 37° C., and absorbancy thereof (OD 655 nm) was measured.

In the results of B of FIG. 2, courses with the passage of time of dye permeation through hepatocytes layers formed by conventional methods on transwell filters are indicated by the white circles ○, while courses of dye permeation through hepatocytes layers formed by the methods of this invention are indicated by black circles ●. All measurements were repeated three times, and measured values were converted to relative values in which the value of a control sample after 30 minutes was counted as 1, and a mean ± a standard deviation were calculated and plotted on the graph.

It is clear from the results in FIG. 2 above that the hepatocytes monolayers treated with staurosporine showed much less permeation of dye than that of the untreated cell layers. This shows that tightness between cells is greatly enhanced by treatment thereof with staurosporine.

The effects achieved by this invention are that 1) a close, confluent continuous monolayer sheet structure of primary hepatocytes is provided, 2) the aforementioned monolayer sheet structure can be formed within 24 hours through simple operations, and 3) the monolayer sheet structure of this invention can be used preferably for construction of artificial internal organs and bioreactors to which confluent monolayer sheet structure of hepatocytes are suitable, and for cell polarity tests by using transwells.

What is claimed is:

1. A monolayer sheet structure comprising a confluent monolayer comprising primary hepatocytes cultured on a substrate in sheet form, wherein said monolayer sheet structure of primary hepatocytes is produced by treating the hepatocytes with a protein-phosphorylation inhibitor having an indolo [2,3-a] carbazole skeleton during formation of the monolayer.

2. The monolayer sheet structure according to claim 1, wherein the protein phosphorylation inhibitor is staurosporine.

3. The monolayer sheet structure according to claim 1, wherein the protein-phosphorylation inhibitor is at least one member selected from the group consisting of K252a, K252b, KT5720, and KT5823.

4. The monolayer sheet structure according to claim 1, wherein the protein-phosphorylation inhibitor is at least one member selected from the group consisting of KT5926, UCN-01, UCN-01-Me, RK-286c, and CGP41251.

5. A monolayer sheet structure consisting of a confluent monolayer comprising primary hepatocytes cultured on a substrate in sheet form, wherein
said monolayer sheet structure of primary hepatocytes is produced by treating the hepatocytes with a protein-phosphorylation inhibitor having an indolo [2,3-a] carbazole skeleton during formation of the monolayer.

6. A method of manufacturing a monolayer sheet structure comprising culturing primary hepatocytes on a culture substrate in sheet form to produce a confluent monolayer, and
treating the hepatocytes with a protein-phosphorylation inhibitor having an indolo [2,3-a] carbazole skeleton during formation of the monolayer to form the monolayer sheet structure of primary hepatocytes.

7. The method according to claim 6, wherein the protein-phosphorylation inhibitor is staurosporine.

8. The method according to claim 6, wherein the protein-phosphorylation inhibitor is at least one member selected from the group consisting of K252a, K252b, KT5720, and KT5823.

9. The method according to claim 6, wherein the protein-phosphorylation inhibitor is at least one member selected from the group consisting of KT5926, UCN-01, UCN-01-Me, RK-286c, and CGP41251.

10. The method according to clam 6, further comprising isolating primary hepatocytes from livers or liver sections by a collagenase perfusion method.

11. The method according to claim 6, further comprising suspending hepatocytes in an animal cell culture medium containing at least one physiologically active hormone.

12. The method according to claim 6, further comprising seeding the hepatocytes on the culture substrate.

13. The method according to claim 6, further comprising subjecting the hepatocytes to a standing culture in the presence of $CO_2$.

14. The method according to claim 13, wherein the subjecting is performed for a time period up to 24 hours.

15. The method according to claim 13, further comprising exchanging a medium of the standing culture with a second culture medium after 4 hours of subjecting the hepatocytes to the standing culture in the presence of $CO_2$.

16. The method according to claim 6, further comprising dissolving the protein-phosphorylation inhibitor in an organic solvent.

17. The method according to claim 6, further comprising dissolving the protein-phosphorylation inhibitor in dimethylsulfoxide.

18. The method according to claim 6, wherein the protein-phosphorylation inhibitor is present at a concentration of from 10 to 50 nM.

* * * * *